United States Patent [19]

Sakamoto et al.

[11] Patent Number: 4,536,387
[45] Date of Patent: Aug. 20, 1985

[54] ANTI-CANCER DEVICE

[75] Inventors: Izumi Sakamoto; Kunihiko Takagi, both of Kyoto, Japan

[73] Assignee: Unitika Ltd., Hyogo, Japan

[21] Appl. No.: 466,190

[22] Filed: Feb. 14, 1983

[30] Foreign Application Priority Data

Feb. 12, 1982 [JP] Japan ................... 57-21924
Nov. 8, 1982 [JP] Japan ................. 57-197147

[51] Int. Cl.³ .......... A61K 9/22; A61K 9/26; A61K 9/70; A61L 15/03
[52] U.S. Cl. ........................ 424/14; 424/15; 424/16; 424/19; 424/22; 424/27; 424/28; 424/32; 424/35; 424/36; 424/37; 424/78; 514/774; 514/777; 514/781
[58] Field of Search ............ 424/14, 16, 28, 37, 424/360

[56] References Cited

U.S. PATENT DOCUMENTS

| | | | |
|---|---|---|---|
| 2,487,975 | 11/1949 | Koree | 424/360 |
| 2,669,537 | 2/1954 | Thompson | 424/360 |
| 2,961,374 | 11/1960 | Lieb et al. | 424/360 |
| 3,009,856 | 11/1961 | Bonce | 424/360 |
| 3,089,815 | 5/1963 | Lieb et al. | 424/360 |
| 3,749,774 | 7/1973 | Schleyerbach et al. | 424/360 |
| 3,932,624 | 1/1976 | Fulton | 424/360 |
| 4,321,117 | 3/1982 | Kaetsu et al. | 424/19 X |
| 4,359,483 | 11/1982 | Kaetsu et al. | 424/19 X |
| 4,411,754 | 10/1983 | Kaetsu et al. | 424/19 X |
| 4,444,753 | 4/1984 | Saikawa et al. | 424/98 |

FOREIGN PATENT DOCUMENTS

| | | | |
|---|---|---|---|
| 53-34915 | 3/1978 | Japan | 424/360 |
| 584497 | 1/1947 | United Kingdom | 424/360 |
| 642380 | 8/1950 | United Kingdom | 424/360 |

Primary Examiner—Shep K. Rose
Attorney, Agent, or Firm—Sughrue, Mion, Zinn, Macpeak & Seas

[57] ABSTRACT

An anti-cancer device having an anti-cancer drug and a blood coagulation factor fixed to a structure. This anti-cancer device is used in transcatheter arterial embolization and needle therapy with advantage and slowly releases the anti-cancer drug over an extended period by staying in the cancer tissue and its nearby area.

54 Claims, No Drawings

ANTI-CANCER DEVICE

FIELD OF THE INVENTION

The present invention relates to an anti-cancer device, and more particularly, to an anti-cancer device that can be used with advantage in treatment and diagnosis of cancers or tumors, such as transcatheter arterial embolization or needle therapy.

BACKGROUND OF THE INVENTION

Transcatheter arterial embolization has recently been recognized as an effective method for treating liver cancer and breast cancer. According to this method, one end of a catheter is inserted into a nutrient artery leading to the cancer or tumoral tissue and a material that occludes the nutrient artery is injected through the other end of the catheter to stop the blood flow. This necroses the cancer or tumor tissue since it is not supplied with additional nutrient. Commonly assigned Japanese Patent Application (OPI) Nos. 135214/79 and 58163/80 (the symbol OPI as used herein means an unexamined published Japanese patent application) and U.S. Pat. No. 4,265,233 proposed materials for wound protection and healing that have blood coagulation Factor XIII and thrombin fixed thereto. It has been reported (as in the 18th Conference of Japanese Society for Artificial Organs and Tissues) that these materials are effectively used as occluding materials in transcatheter arterial embolization. But one great disadvantage of the transcatheter arterial embolization technique is that it cannot be supplemented with chemotherapy which is another effective way to treat cancers or tumors. After transcatheter arterial embolization, administering an anti-tumor agent orally or by injection is meaningless since the nutrient artery has been closed to prevent the agent from reaching the cancer or tumoral tissue. Therefore, if transcatheter arterial embolization is effected, the surgeon either abandons chemotherapy or occludes the nutrient artery after injecting an anti-cancer agent through a catheter inserted into the artery. But this two-step method is not very effective since the applied anti-cancer agent runs away in an extremely short time to sites other than the target cancer or tumor tissue; for one thing, the agent is usually administered in solution and its amount is not very great, and for another, the nutrient artery has not been completed occluded. Therefore, the incompatibility with chemotherapy, the biggest problem with the transcatheter arterial embolization technique, is yet to be solved, and a new pharmaceutical preparation that is free from this defect is in great demand.

There is another technique that is considered to be promising as a method of treating cancer, and this is needle therapy. The term needle therapy as conventionally used means drawing body fluids through a hollow needle, but needle therapy as used hereunder relates to a method of examining and treating cancer or tumor tissue. Examination by needle therapy is generally referred to as biopsy and consists of examining a sample of body tissues. For application to the examination of cancer or tumor tissues, this technique consists of collecting a doubtful tissue with a needle and subjecting it to diagnostic examination. Two problems have been pointed out in connection with this technique. One is that the cancer or tumor tissue collected on the tip of the needle may contaminate normal tissue as the needle is withdrawn, and no effective method is available for avoiding this trouble. The other problem is bleeding. Unlike transcatheter arterial embolization wherein a catheter is inserted into a blood vessel, needle therapy involves piercing the body with a needle to reach the target tissue and causes bleeding from the damaged site. If the damaged site is normal, bleeding stops spontaneously and the damaged blood vessel is repaired in a fairly short period and there will be no adverse postoperative effect. But the cancer or tumoral tissue lacks ability to stop bleeding and repair a damaged blood vessel, and this is usually so with the neighboring tissues. Therefore, they have a great tendency to bleed during needle therapy and once they bleed, it is difficult to stop the bleeding. If serious bleeding is expected, the very operation by needle therapy must be abandoned. The problem of bleeding is particularly great with a spleen, which is rarely subjected to needle therapy. In most cases of needle therapy, the needle with the target tissue on its tip is withdrawn while a proper method is being applied to stop bleeding. The common method of achieving this object is to inject an aqueous solution of thrombin during the withdrawing of the needle. But even this method is not completely satisfactory since the ability of thrombin to stop bleeding is not very great and the thrombin, being liquid, runs away from the site that is damaged and needs repairing. The second type of needle therapy which is directed to treatment of cancer or tumor tissues consists of directly injecting an anti-cancer agent through a needle into the target tissue. Since the needle currently used in this techniuqe is as fine as 19G to 23G, the only anti-cancer agent that can be inejcted is antibiotics and other drugs in solution. But if the anti-cancer agent in solution is injected through the needle, it immediately departs from the target tissue and the purpose of topical application of the drug is not achieved. Therefore, it has long been desired to develop a therapeutic preparation that can be injected through a very fine needle (19-23G) into the target tissue and the area around the injection pathway and which stays at the injected site as long as it slowly releases the active agent.

SUMMARY OF THE INVENTION

Therefore, a general object of the present invention is to provide an anti-cancer device that can be used in both transcatheter arterial embolization and needle therapy. When the device is used in transcatheter arterial embolization, it is capable of rapid and reliable occlusion of the blood vessel and lets the active ingredient effectively act on the target cancer or tumor tissue for an extended period. When the device is applied to needle therapy, it stops bleeding quickly and reliably and repairs the damaged blood vessel in an early period. Furthermore, the device permits the active substance to work effectively on the cancer or tumor tissue that is most likely to contaminate the area around the route along which the needle is to be withdrawn.

As a result of various studies to attain the stated object, the present inventors have found that a structure having an anti-cancer drug and a blood coagulation factor fixed thereto has high ability to occlude a blood vessel, stop bleeding and repair a damaged blood vessel. The inventors have also found that once it has reached the target site (the cancer or tumor tissue to be treated), the structure stays there as well as the nearby area without being washed away with blood or body fluids, and keeps slowly releasing the anti-cancer drug over an extended period. The present invention therefore provides an anti-cancer device comprising a structure comprised of a polymer, an anti-cancer drug, and a blood coagulation factor, wherein the anti-cancer drug and blood coagulation factor are fixed to the structure in such a manner as to be capable of sustained release from the structure.

Within this specification, the term "device" refers to any structure such as fibrous assembly, sponge, powder, monofilament, film and microcapsule, having fixed thereto an anti-cancer drug and a blood coagulation factor, the anti-cancer drug and blood coagulation factor being fixed to the structure in such a manner as to permit its sustained release.

DETAILED DESCRIPTION OF THE INVENTION

The structure used in the present invention may be made up of synthetic polymers such as silicone, polyesters, polyamides, polyurethanes, polyacrylonitrile, polyacrylamide, polyacrylic acid esters, polyethylene, polypropylene, polyvinyl chloride and polyvinyl alcohol; cellulosic materials and their derivatives such as cotton, hemp, pulp, ethyl cellulose and cellulose acetate; regenerated cellulose such as viscose rayon and caprammonium rayon; and various bioabsorbable materials. Illustrative bioabsorbable materials include polysaccharides such as amylose, oxidized cellulose, dextran, chitin and pullulan; collagen, gelatin, polyglutamic acid and their ester derivatives with hydroxyethylbenzyl, etc.; polyamino acids such as polylysine, polyaspartic acid and polyphenylalanine; polyglycolic acid, polylactic acid, glycolic acid-polylactic acid copolymer; and polyesters of succinic acid and polyesters of oxalic acid. Because of their nontoxicity to humans, silicone, cellulose derivatives and bioabsorbable materials are preferred.

In many cases, the anti-cancer device of the present invention is not taken out of the human body after it is injected into the target site. Therefore, the structure is preferably made up of a material that is not left unabsorbed by the tissue, and in this respect, bioabsorbable materials such as gelatin, chitin, collagen, amylose, polyglycolic acid, polylactic acid and oxidized cellulose are particularly preferred, more preferably gelatin, chitin and oxidized cellulose.

The anti-cancer drug as used in the present invention means those chemotherapeutic agents commonly called anti-tumor agents and those which are referred to as immunotherapeutics or immunoactivators. Amont the first type of drugs are included alkylating agents such as Nitrogen mustards, nitromin, chlorambucil, cyclophosphamide, melphalan, uracil mustard, mannomustine, dopan, BCNU, triethylenemelamine, thio-TEPA, Aza-TEPA, threnimone, inprocuon, busulfan, dimethylmilelane, piposulfan, ethoglucide, epoxypropidine, epoxypiperazine, hexamethylmelamine, dibromomannitol, pipobroman, CCNU, methyl-CCNU, chlorozotocin, GANU, MCNU, ACNU, TA-077 and fosamid; antimetabolites such as folic acid, aminopterin, methotrexate, guanine, 8-azaguanine, 6-mercaptopurine, azathioprine, uracil, 5-fluorouracil, cytarabine, azaserine, diazamycin, BHAC, SM108, cispuracham, cytosine arabinoside, tegaful, HCFU, 5'DFUR, TK-117 and cyclotidine; antibiotics such as actinomycin D, cyclomycin, mitomycin C, daunomycin, bleomycin, cromomycin, carzinophyllin, macrocinomycin, neothramycin, thalisomycin, sporamycin, saframycin, ansamytocin, DON, macromomycin, nogaromycin, 7-o-methylnogallol-4'-epiadriamycin, streptozotocin, 4-demethoxydaunorubicin and mitozanthron; synthetic agents such as 5-HP and IQ-1; plant components such as thiotepa, cyclophosphamide, doxorubicin, daunorubicin and neocarzinostain; and Hg-hematoporphyrine, Co-protoporphyrine, stillbestrol, hydroxyurea, procarbazine, methylglyoxalbisguanylhydrazone, L-asparaginase and TNF. These chemotherapeutic agents may be used either alone or in combination. Commonly, one alkylating agent, one antimetabolite and one antibiotic are combined, and more commonly, cyclophosphamide, 5-fluorouracil and mitomycin or bleomycin are combined.

Illustrative immunotherapeutics or immunoactivators include thymic hormones and their related substances, BCG, skeletal cell walls and their methanol-insoluble fractions, microorganism such as *Corynebacterium parvum* and OK-432 and their components; polysaccharides such as picivanil, lentinan, SPG, mannan, levan and glucan; muramyl dipeptide and its derivatives; levamisole, pestatin, isoprinocin, NPT 15392, azimecrin, transfer factors, lymphokain, immuno-RNA, interferons and their inducers and vaccines such as Maruyama vaccine. These immunotherapeutics or immunoactivators may be used either alone or in combination. Commonly, they are used in combination with the above-listed anti-tumor agents.

In the present invention, bleomycin, mitomycin C, adriamycin and 5-fluorouracil are preferred since their effectiveness in controlling cancer are widely recognized and their high toxicity requires topical rather than systemic administration.

Examples of the blood coagulation factor that can be used in the present invention include coagulation factors I, II, III, IV, V, VII, VIII, IX, X, XI, XII and XIII, as well as prekallikrein, high-molecular weight kininogen and thrombin. These factors may be used either alone or in combination. In the present invention, coagulation factor XIII (hereunder abbreviated to F XIII) and thrombin are preferred, and the combination of F XIII and thrombin is most preferred. F XIII is referred to as a fibrin stabilizing factor and promotes the stabilization of instable fibrin by forming isopeptide linkages between the fibrin molecules. F XIII is isolated from the blood or placenta of man and cattle. For application to a human, the use of F XIII derived from humans is preferred. Thrombin is a protease capable of converting fibrinogen to fibrin. It is isolated from the blood of man, cattle, swine, etc., and for application to man, the use of human thrombin is preferred.

The anti-cancer drug and blood coagulation factor that are used in the present invention can be fixed to the structure by bonding, adsorption or encapsulation. The anti-cancer drug and blood coagulation factor can be bonded to the structure by known methods of covalent bonding and ion bonding as described in O. Zaborsky, "Immobilized Enzymes", CRC Press, 1973. The anti-cancer drug and blood coagulation factor may be adsorbed on the structure either by physical adsorption or entrapping. For encapsulation, the anti-cancer drug and blood coagulation factor may be enclosed with an outer wall of the structure-making material by a known method of microcapsulation.

More specifically, to prepare the anti-cancer device of the present invention, the anti-cancer drug and blood coagulation factor may be bound to the structure by either of the following methods. When the anti-cancer drug and blood coagulation factor each contain a functional group capable of forming a covalent or ionic bond (e.g., an amino group or carboxyl group), a solution containing them may be used to treat the structure containing functional groups capable of covalent bonding or ionic bonding with these functional groups, and by so doing, they are fixed to the structure. When the structure contains few or no functional groups capable of covalent bonding or ionic bonding to the functional group in the anti-cancer drug or blood coagulation factor, the latter may be bonded to the structure after chemically introducing the necessary group into the structure. If the anti-cancer drug or blood coagulation factor has no functional group, it may also be used after chemically introducing a functional group, but in most cases, this method is not advantageous since the chemical reaction used to introduce the necessary functional group impairs the therapeutical characteristics of the anti-cancer drug or blood coagulation factor. In the case of covalent bonding, it is preferred to use a dehydrocondensation agent such as dicyclohexyl carbodiimide, 1-cyclohexyl-3-(2-morpholinoethyl)carbodiimide-metho-p-toluenesulfonate.

In this case the dehydro-condensation agent is dissolved in an amount of about 0.1 to 20% by weight, preferably about 1 to 10% by weight, in water or a mixture of water with a water-miscible solvent such as methyl alcohol, ethyl alcohol, propyl alcohol, dioxane, tetrahydrofuran, dimethylformamide or dimethyl sulfoxide. A structure is treated with a mixed solution of the dehydro-condensation agent solution and the anti-cancer drug and blood coagulation factor solution, or first with the dehydro-condensation agent solution and subsequently with the anti-cancer drug and blood coagulation factor solution or vice versa, at a temperature of about −20° C. to about 60° C., preferably 0° to 40° C., for about 10 min. to about 72 hrs., preferably for 30 min. to 24 hrs.

Fixation of anti-cancer drug and blood coagulation factor to the structure having a functional group or an ion exchange group to thereby covalently or ionically bond is performed by treating the structure with a solution of the anti-cancer drug and blood coagulation factor. Fixation of anti-cancer drug and blood coagulation factor is carried out by treating the structure with a solution containing the anti-cancer drug and blood coagulation factor, or by first treating it with a solution of anti-cancer drug and subsequently with a solution of blood coagulation factor, or in the reverse order.

In these methods, in view of ease of operation the method of treating the structure with solvent containing both the anti-cancer drug and blood coagulation factor is preferred, but in view of the prevention of the condensation and activity reduction thereof the method of treating separately it with a solution containing anti-cancer drug or a solution containing blood coagulation factor is preferred. Anti-cancer drug and blood coagulation factor dissolve in water or a mixture of water with water-miscible solvent such as methanol, ethanol, propanol, acetone, tetrahydrofuran, dioxane, dimethyl sulfoxide or dimethylformamide. A suitable temperature for the fixation is about −20° C. to 70° C., preferably about 0° to 40° C., and suitable treating time is about 1 min. to 48 hrs., preferably about 2 min. to 24 hrs. In fixing anti-cancer drug and blood coagulation factor, the pH of the solution should be adjusted to about 3 to about 10, preferably 4 to 9.

In producing the anti-cancer device of this invention, anti-cancer drug and blood coagulation factor can be fixed to the structure in the form of a monofilament, a fibrous assembly, a film, a microcapsule, a powder or a sponge or the like by adsorption in the following manner. As a form of these structures, a powder and a sponge are preferred. Adsorption of anti-cancer drug and blood coagulation factor can be carried out by treating the structure with solvent containing the anti-cancer drug and blood coagulation factor which are dissolved, emulsified or suspended in a solvent capable of wetting the structure, or by first treating it with a solution containing anti-cancer drug and subsequently with a solution containing blood coagulation factor, or in the reverse order.

In these methods, in view of ease of operation the method of treating the structure with solvent containing both the anti-cancer drug and blood coagulation factor is preferred, but in view of the prevention of the condensation and activity reduction thereof the method of treating separately it with a solution containing anti-cancer drug or a solution containing blood coagulation factor is preferred. Adsorption is carried out at a temperature of about −20° C. to 60° C., preferably about 0° to 40° C., for a period of about 1 min. to 72 hrs., preferably about 3 min. to 24 hrs. Suitable solvents are water and mixtures of water and water-miscible solvents such as methanol, ethanol, propanol, acetone, tetrahydrofuran, dioxane, dimethyl sulfoxide and dimethylformamide.

Anti-cancer device of this invention can also be produced by fixing anti-cancer drug and blood coagulation factor by entrapping. Entrapping comprises entrapping anti-cancer drug and blood coagulation factor in the fine lattices of a gel or in a polymeric film. Suitable materials used in the adsorption or entrapping method are adsorbable materials such as collagen, gelatin, polyglycolic acid, polylactic acid, a glycolic acid/lactic acid copolymer, polyglutamic acid, amylose and chitin.

The amount of anti-cancer drug and blood coagulation factor fixed to the structure varies over a wide range in accordance with a type of sustained release, the time for which the anti-cancer device is used and the form of the anti-cancer device.

However, generally, the amount of the anti-cancer drug fixed is 0.001 to 1,000 mg per 1 mg of the structure and the amount of the blood coagulation factor fixed is 0.001 to 100 mg per 1 mg of the structure. The preferred amounts of the anti-cancer drug and blood coagulation factor fixed to the structure vary in accordance with a kind thereof. For example, the amounts of mitomycin C, bleomycin, adriamycin, 5-fluorouracil, F XIII and thrombin are preferably 0.001 to 200 mg, 0.01 to 100 mg, 0.001 to 200 mg, 0.001 to 1,000 mg, 0.001 to 50 mg and 0.01 to 100 mg per 1 mg of the structure, respectively. When the anti-cancer device is allowed to stand in human plasma at 37° C., the fixed anti-cancer drug and blood coagulation factor can be released from the anti-cancer device for 1 hour or more, 5 hours or more, 10 hours or more, 24 hours or more, or 2 days or more.

The anti-cancer device of the present invention may be produced by methods other than bonding or adsorbing the anti-cancer drug and blood coagulation factor to the structure or entrapping the former in the latter. For instance, the anti-cancer drug and blood coagulation factor may be bonded or adsorbed on or entrapped in the raw material of the structure, and the resulting product is processed into a predetermined form of the structure. In one embodiment of this modification, the anti-cancer drug is first bonded or adsorbed on, or entrapped in, a polymeric material to form the desired structure which is given the necessary treatment into the anti-cancer device of the present invention. Alternatively, a structure to which the anti-cancer drug is fixed and another structure to which the blood coagulation factor is fixed may be assembled to form the anti-cancer device of the present invention. In this case, the two structures, instead of being assembled, may be kept separate until use, whereupon they are mixed by suspending in a physiological saline solution and serve as the anti-cancer device of the present invention.

In the production of the anti-cancer device of this invention, a calcium ion which participates in the activation of the blood coagulation reaction can be fixed together with the anti-cancer drug and blood coagulation factor. The calcium ion is generally added to the structure as calcium chloride in an amount of 0.1 $\mu$mol to 1 mmol, preferably 0.5 $\mu$mol to 200 $\mu$mol.

In addition to the anti-cancer drug and blood coagulation factor, various pharmaceuticals may be fixed to the structure, and suitable pharmaceuticals include protease inhibitors such as antiplasmin, albumin and alpha$_2$-macroglobulin; plasma proteins such as ceruloplasmin, haptoglobin and cold insoluble globulin (CIG); and fibronectin, antibiotics, antivirals, sulfamides and antiinfectives. CIG and fibronectin are believed to have affinity for cancer tissues or ability to inhibit their growth, and hence, together with the anti-cancer device of the present invention, are expected to enhance the effect of the anti-cancer drug. Antiplasmin is an inhibitor of plasmin, a fibrinolytic enzyme, and also enhances the effectiveness of the anti-cancer device of the present invention. Preferred antiplasmins are $\epsilon$-aminocaproic acid and tranexamic acid.

Since such pharmaceutical fixed to the structure together with anti-cancer drug and blood coagulation factor varies in a wide range in accordance with a kind of pharmaceutical, the desired effects and the time of which the anti-cancer device is used, it is not practical to determine the range of the amount of the pharmaceutical. However, generally, the amount of the pharmaceutical fixed thereto is 1 microgram to 100 milligram per 1 g of the anti-cancer device, preferably 10 microgram to 10 milligram.

The anti-cancer device of the present invention is preferably used in treating cancers or tumors, and it is particularly preferred to use it in transcatheter arterial embolization or needle thereapy. In transcatheter arterial embolization, one end of a catheter is inserted into a nutrient artery leading to the target cancer or tumor tissue and a suspension of the anti-cancer device in a physiological saline solution is injected from the other end of the catheter. Part of the injected device reaches not only the target tissue but also the nearby tissue and stays there, and the other part of the device, serving as an occluding material, stays within the nutrient vessel to occlude it. The occluded vessel will not open again. The anti-cancer device with sustained release staying on the target tissue, its neighboring area and within the occluded vessel releases the effective compound to topically act on the cancer or tumor tissue for an extended period, thus accomplishing rapid and reliable necrosis of the malignant tissue. This means that a rapid and reliable operation by transcatheter arterial embolization is possible with the anti-cancer device with sustained release of the present invention and that it can be supplemented with a chemotherapeutic technique that is conventionally incompatible with the transcatheter arterial embolization technique.

In needle therapy, a needle is pierced through the skin to the target cancer to tumor tissue, and the necessary amount of a suspension in a physiological saline of the anti-cancer device of the present invention is injected into the target tissue, and then the needle is withdrawn as more suspension is introduced. In consequence, the anti-cancer device of the present invention is topically administered to the target tissue and the tissue about the needle's route, and because of the fibrin network formed by the blood coagulation factor fixed to the structure, the device stays in the injected area. The device immediately stops the bleeding and repairs the damage site of the blood vessel, and at the same time, it slowly releases the active compound to work effectively on the cancer or tumor tissue over a prolonged period. The anti-cancer device that has been injected as the needle is being withdrawn and which stays on the tissue around the needle's path also immediately stops the bleeding of the damaged blood vessel in the nearby tissue and reparis the damage. At the same time, the device releases the active compound that has long-lasting effectiveness on the cancer or tumor cells that contaminate the tissue around the needle's pathway.

As described in the foregoing, the anti-cancer device of the present invention is effectively used in transcatheter arterial embolization and needle therapy, wherein it serves as an excellent agent that not only occludes blood vessels but also lets an anti-cancer drug be released over a prolonged period. Since the anti-cancer device of the present invention is administered topically, the problem that may be caused by the strong toxicity of the drug can be avoided. The advantage of the anti-cancer device of the present invention is also apparent when it is used in therapies other than transcatheter arterial embolization and needle therapy. For instance, it may be dusted over a cancer tissue that has been exposed by a surgical operation; the applied device immediately sticks to the tissue and will not be washed away by blood or body fluids.

The present invention is now described in greater detail by reference to the following examples which are given here for illustrative purposes only and are by no means intended to limit the scope of the invention.

EXAMPLE 1

Two hundred milligrams of absorbable gelatin powder (Gelfoam, Japan Upjohn Ltd.) was immersed for 5 minutes at room temperature in a mixture of 4 ml of an aqueous Fibrogamin solution (prepared by dissolving a bottle of concentrated dry human F XIII of Hoechst Aktiengesellschaft in 4 ml of water), 5 ml of a physiological saline solution of thrombin (prepared by dissolving a bottle of concentrated dry human thrombin of The Green Cross Corporation in 5 ml of physiological saline) and 4 ml of an aqueous solution of mitomycin C (20 mg/4 ml), and the resulting suspension was freeze-dried at $-30°$ C. for 15 hours to prepare a Gelfoam wherein 240 units of F XIII, 500 units of thrombin and 20 mg of mitomycin C were fixed to gelatin through ionic bonding, entrapping and adsorption.

A loop of medical silicone tube (length: 34 cm long, ID: 4 mm) in a room (2° C.) was filled first with a mixture of ACD stored blood (2 ml) and 10 wt% aqueous CaCl$_2$ solution (1 ml), then with 20 mg of the previously prepared Gelfoam. The resulting sample was placed on a rotary plate inclined at an angle of 23 degrees and was rotated at 16 rpm. One minute later, a clot formed, and the rotation of the plate was stopped. One hour later, a paper disc for testing antibiotics (8 mm in diameter) produced by Toyo Engineering Works, Ltd. was thoroughly immersed in the blood or placed into intimate contact with the clot in the loop and subjected to a culture test with *Bacillus subtilis* ATCC 6633 by the cylinder-tray method. The size of the resulting inhibition zone indicated that the concentration of mitomycin C in blood for the first hour was 10 μg/mg. The same measurement was made 5 hr. 10 hr, 24 hr, 1.5 days, 2 days and 3 days after the stoppage of the rotation of the blood sample. The respective concentrations of mitomycin C in blood were 15 μg/mg, 21 μg/mg, 41 μg/mg, 82 μg/mg, 112 μg/mg and 198 μg/mg.

COMPARATIVE EXAMPLE 1

Twenty milligrams of Gelfoam having mitomycin C fixed to gelatin was prepared by repeating the procedure of Example 1 except that neither F XIII nor thrombin was used. It was placed on a rotary loop as in Example 1 and subjected to a coagulation test, followed by measurement of the concentration of mitomycin C in blood. No clot formed even after 3 hours of rotation of the loop, and the concentration of mitomycin C in blood at that time was 600 μg/ml. This indicates that having no sustained release, the Gelfoam released almost all of mitomycin C into the blood within 3 hours.

EXAMPLE 2

Two hundred milligrams of absorbable gelatin powder (Gelfoam, Japan Upjohn Ltd.) was immersed in 4 ml of an aqueous Fibrogamin solution (prepared by dissolving a bottle of concentrated dry human F XIII of Hoechst Aktiengesselschaft in 8 ml of water) for 3 minutes at room temperature, and then freeze-dried at −30° C. for 15 hours. The freeze-dried product was immersed for 5 minutes at room temperature in a suspension of 25 mg of 5-fluorouracil in 4 ml of dimethylformamide, and freeze-dried at −30° C. for 15 hours to prepare a Gelfoam wherein 240 units of F XIII and 20 mg of 5-fluorouracil were fixed to gelatin through ionic bonding, entrapping and adosrption. Twenty milligrams of the sample was placed on a rotary loop and subjected to a coagulation test as in Example 1. One minute and a half after the loop started to rotate, a clot formed. The rotation of the loop was stopped and 50 μg of blood or clot was sampled 5 hr, 10 hr, 24 hr, 1.5 days, 2 days and 3 days later. The samples were freeze-dried and their 5-fluorouracil concentrations in blood were determined by measuring the weight of 5-fluorouracil in the respective samples by the oxygen flask combustion method using a mixture of sodium hydroxide and water as an absorbent: the respective values were 12 μg/mg (5 hr), 17 μg/mg (10 hr), 38 μg/mg (24 hr), 78 μg/mg (1.5 days), 101 μg/mg (2 days and 162 μg/mg (3 days).

EXAMPLE 3

Twenty milligrams of chitin powder having 240 units of F XIII, 500 units of thrombin and 20 mg of mitomycin C fixed to chitin by ionic bonding, entrapping and adsorption was prepared by repeating the procedure of Example 1 except that the Gelfoam was replaced by chitin powder (mol. wt. 1,000,000, Kyowa Yushi Co., Ltd.). It was subjected to a coagulation test with a rotary loop as in Example 1. One minute after the loop started to rotate, a clot formed and the blood in the loop became no longer fluid. The rotation of the loop was stopped and the concentration of mitomycin C in blood was measured 1 hr, 5 hr, 10 hr, 24 hr, 1.5 days, 2 days and 3 days later: the respective values were 8 μg/ml, 14 μg/ml, 19 μg/ml, 38 μg/ml, 78 μg/ml, 108 μg/ml and 178 μg/ml.

EXAMPLE 4

A sheet of absorbable gelatin sponge (Spongel, Yamanouchi Pharmaceutical Co., Ltd.) measuring 2.5 cm×5 cm×0.5 cm was immersed for 5 minutes at room temperature in a solution having 200 mg of bleomycin and 20 mg of 1-cyclohexyl-3-(2-morpholinoethyl)carbodiimide-metho-p-toluenesulfonate dissolved in a physiological saline solution of thrombin (prepared by dissolving a bottle of thrombin in 10 ml of physiological saline), and the resulting suspension was freeze-dried at −30° C. for 15 hours to produce a Spongel wherein 500 units of thrombin and 190 mg of bleomycin were fixed to gelatin through covalent bonding, adsorption and entrappping. Twenty milligrams of the Spongel was placed on a rotary loop and subjected to a coagulation test as in Example 1. One minute after the loop was started to rotate, a clot formed. The rotation of the loop was then stopped and the concentration of bleomycin in blood was measured 1 hr, 5 hr, 10 hr, 24 hr, 1.5 days, 2 days and 3 days later: the respective values were 5 μg/mg, 7 μg/mg, 11 μg/mg, 21 μg/mg, 41 μg/mg, 62 μg/mg and 123 μg/mg.

EXAMPLE 5

One gram of ethyl cellulose beads (ca. 250 microns in diameter) were immersed in 100 g of 2 wt% aqueous aminoacetal solution at 60° C. for 8 hours. The beads were recovered, washed with water, immersed in 100 g of a 4 wt% acetone solution of methyl vinyl ether-maleic anhydride copolymer (Gantrez AN-169 of GAF Corporation) for 2 hours at room temperature and washed with acetone. The washed beads were dried and 150 mg of them was immersed in 4 ml of an aqueous Fibrogamin solution (prepared by dissolving a bottle of concentrated dry human F XIII of Hoechst Aktiengesselschaft in 9 ml of water) for 3 minutes at room temperature, and then freeze-dried at −30° C. for 15 hours. The freeze-dried product was immersed in a suspension of 25 mg of 5-fluorouracil in 4 ml of dimethylformamide for 5 minutes at room temperature, and freeze-dried at −30° C. for 15 hours to prepare ethyl cellulose beads wherein 240 units of F XIII and 25 mg of 5-fluorouracil were fixed to cellulose primarily by covalent bonding. Twenty milligrams of the sample was placed on a rotary loop and subjected to a coagulation test as in Example 1. One minute and a half after the loop started to rotate, a clot formed. The rotation of the loop was stopped and 50 μg of blood or clot was sampled 5 hr, 10 hr, 24 hr, 1.5 days, 2 days and 3 days later. The samples were freeze-dried and their 5-fluorouracil concentrations in blood were determined by measuring the weight of 5-fluorouracil in the respective samples by the oxygen flask combustion method using a mixture of sodium hydroxide and water as an absorbent: the respective values were 3.5 μg/mg, 5.5 μg/mg, 10.0 μg/mg, 21.5 μg/mg, 31.5 μg/mg and 60.0 μg/mg.

EXAMPLE 6

Two hundred milligrams of nylon sponge cut to lengths of about 500μ was immersed for 5 minutes at room temperature in a mixture of an aqueous Fibrogamin solution (prepared by dissolving a bottle of concentrated dry human F XIII of Hoechst Aktiengesellschaft in 4 ml of water), 4 ml of a physiological saline solution of thrombin (prepared by dissolving a bottle of concentrated dry human thrombin of The Green Cross Corporation in 5 ml of physiological saline) and 4 ml of an aqueous solution of mitomycin C (20 mg/4 ml), and the resulting suspension was freeze-dried at $-30°$ C. for 15 hours to prepare a nylon sponge wherein 200 units of F XIII, 450 units of thrombin and 20 mg of mitomycin C were fixed to nylon through ionic bonding, entrapping and adsorption.

A loop of medical silicone tube (length: 34 cm, ID: 4 mm) in a room (2° C.) was filled first with a mixture of ACD stored blood (2 ml) and 10 wt% aqueous $CaCl_2$ solution (1 ml), then with 20 mg of the previously prepared nylon sponge. The resulting sample was placed on a rotary plate inclined at an angle of 23 degrees and was rotated at 16 rpm. One minute later, a clot formed, and the rotation of the plate was stopped. One hour later, a paper disc for testing antibiotics (8 mm in diameter) produced by Toyo Engineering Works, Ltd. was thoroughly immersed in the blood or placed into intimate contact with the clot in the loop and subjected to a culture test with *Bacillus subtilis* ATCC 6633 by the cylinder-tray method. The size of the resulting inhibition zone indicated that the concentration of mitomycin C in blood for the first hour was 10 $\mu g/mg$. The same measurement was made 5 hr, 10 hr, 24 hr, 1.5 days, 2 days and 3 days after the stoppage of the rotation of the blood sample. The respective concentrations of mitomycin C in blood were 15 $\mu g/mg$, 21 $\mu g/mg$, 41 $\mu g/mg$, 82 $\mu g/mg$, 112 $\mu g/mg$ and 198 $\mu g/mg$.

COMPARATIVE EXAMPLE 2

Twenty milligrams of nylon sponge having mitomycin C fixed to nylon was prepared by repeating the procedure of Example 6 except that neither F XIII nor thrombin was used. It was placed on a rotary loop as in Example 6 and subjected to a coagulation test, followed by measurement of the concentration of mitomycin C in blood. No clot formed even after 3 hours of rotation of the loop, and the concentration of mitomycin C in blood at that time was 600 $\mu g/ml$. This indicates that having no sustained release, the nylon sponge released almost all of mitomycin C into the blood within 3 hours.

EXAMPLE 7

Polyethylene terephthalate beads (ca. 250 microns in diameter) were immersed in a mixture of 10 wt% aqueous polyethyleneimine and methanol whose volume was 5 times as much as that of the aqueous polyethyleneimine, and they were left to stand at room temperature for 30 minutes. A methanol solution of 5 wt% dicyclohexylcarbodiimide whose volume was twice that of the aqueous polyethyleneimine was added, and the beads were held at room temperature for two more hours. The beads were then washed with water, dried, immersed in an acetone solution of 4 wt% methyl vinyl ether-maleic anhydride copolymer at room temperature for 2 hours, and washed with acetone. The washed beads were dried and 200 mg of them was immersed in 4 ml of an aqueous Fibrogamin solution (prepared by dissolving a bottle of concentrated dry human F XIII of Hoechst Aktiengesselschaft in 8 ml of water) for 3 minutes at room temperature, and then freeze-dried at $-30°$ C. for 15 hours. The freeze-dried product was immersed in a suspension of 25 mg of 5-fluorouracil in 4 ml of dimethylformamide for 5 minutes at room temperature, and freeze-dried at $-30°$ C. for 15 hours to prepare polyethylene terephthalate beads wherein 180 units of F XIII and 20 mg of 5-fluorouracil were fixed to polyethylene terephthalate primarily by covalent bonding. Twenty milligrams of the sample was placed on a rotary loop and subjected to a coagulation test as in Example 6. One minute and a half after the loop started to rotate, a clot formed. The rotation of the loop was stopped and 50 $\mu g$ of blood or clot was sampled 5 hr, 10 hr, 24 hr, 1.5 days, 2 days and 3 days later. The samples were freeze-dried and their 5-fluorouracil concentrations in blood were determined by measuring the weight of 5-fluorouracil in the respective samples by the oxygen flask combustion method using a mixture of sodium hydroxide and water as an absorbent: the respective values were 3.0 $\mu g/mg$ (5 hr), 5.0 $\mu g/mg$ (10 hr), 9.5 $\mu g/mg$ (24 hr), 20.0 $\mu g/mg$ (1.5 days), 29.5 $\mu g/mg$ (2 days) and 58.5 $\mu g/mg$ (3 days).

EXAMPLE 8

Nylon beads wherein 180 units of F XIII and 200 mg of 5-fluorouracil were fixed to nylon primarily by covalent bonding were prepared as in Example 7 except that the polyethylene terephthalate beads were replaced by nylon beads (ca. 200 microns in diameter). Twenty milligrams of the beads were subjected to a coagulation test with a rotary loop as in Example 6. One minute after the loop started to rotate, a clot formed and the blood became no longer fluid. The rotation of the loop was then stopped and the concentration of 5-fluorouracil in blood was measured 1 hr, 5 hr, 10 hr, 24 hr, 1.5 days, 2 days and 3 days later: the respective values were 1.5 $\mu g/mg$, 3.5 $\mu g/mg$, 5.5 $\mu g/mg$, 10.5 $\mu g/ml$, 20.5 $\mu g/ml$, 30.0 $\mu g/ml$ and 58.5 $\mu g/ml$.

EXAMPLE 9

Square sheets (500×500$\mu$) of nylon taffeta were immersed for 5 minutes at room temperature in a solution having 200 mg of bleomycin and 20 mg of 1-cyclohexyl-3-(2-morpholinoethyl)carbodiimide-metho-p-toluenesulfonate dissolved in a physiological saline solution of thrombin (prepared by dissolving a bottle of thrombin in 10 ml of physiological saline), and the resulting suspension was freeze-dried at $-30°$ C. for 15 hours to produce a nylon taffeta wherein thrombin and bleomycin was fixed to nylon primarily by covalent bonding. Twenty milligrams of the taffeta was placed on a rotary loop and subjected to a coagulation test as in Example 6. One minute after the loop started to rotate, a clot formed. The rotation of the loop was then stopped and the concentration of bleomycin in blood was measured 1 hr, 5 hr, 10 hr, 24 hr, 1.5 days, 2 days and 3 days later: the respective values were 2.0 $\mu g/mg$, 4.0 $\mu g/mg$, 6.0 $\mu g/mg$, 10.5 $\mu g/mg$, 21.5 $\mu g/mg$, 31.0 $\mu g/mg$ and 59.5 $\mu g/mg$.

While the invention has been described in detail and with reference to specific embodiments thereof, it will be apparent to one skilled in the art that various changes and modifications can be made therein without departing from the spirit and scope thereof.

What is claimed is:

1. A method of transcatheter arterial embolization and needle therapy comprising injecting a patient with composition useful for transcatheter arterial embolization and needle therapy comprising:
   (a) a polymer, wherein said polymer has fixed thereto;

(b) an anti-cancer drug; and
(c) a blood coagulation factor, wherein said anti-cancer drug and said blood coagulation factor are fixed to said polymer so as to be capable of sustained release from the polymer at the site of injection.

2. The method as claimed in claim 1, wherein said polymer is a synthetic polymer.

3. The method as claimed in claim 2, wherein said synthetic polymer is silicone.

4. The method as claimed in claim 1, wherein said polymer is selected from the group consisting of cellulosic material, cellulosic material derivative and regenerated cellulose.

5. The method as claimed in claim 4, wherein said cellulosic material derivative is ethyl cellulose.

6. The method as claimed in claim 1, wherein said polymer is bioabsorbable material.

7. The method as claimed in claim 6, wherein said bioabsorbable material is polysaccharide.

8. The method as claimed in claim 7, wherein said polysaccharide is amylose.

9. The method as claimed in claim 7, wherein said polysaccharide is oxidized cellulose.

10. The method as claimed in claim 7, wherein said polysaccharide is chitin.

11. The method as claimed in claim 6, wherein said bioabsorbable material is collagen.

12. The method as claimed in claim 6, wherein said bioabsorbable material is gelatin.

13. The method as claimed in claim 6, wherein said bioabsorbable material is polyamino acid.

14. The method as claimed in claim 13, wherein said polyamino acid is polyglycolic acid.

15. The method as claimed in claim 13, wherein said polyamino acid is polylactic acid.

16. The method as claimed in claim 1, wherein the polymer is in the form of a fibrous assembly.

17. The method as claimed in claim 16, wherein said fibrous assembly is an assembly of oxidized cellulose fiber.

18. The method as claimed in claim 16, wherein said fibrous assembly is an assembly of gelatin fiber.

19. The method as claimed in claim 16, wherein said fibrous assembly is an assembly of chitin fiber.

20. The method as claimed in claim 1, wherein said polymer is in the form of a sponge.

21. The method as claimed in claim 20, wherein said sponge is oxidized cellulose sponge.

22. The method as claimed in claim 20, wherein said sponge is gelatin sponge.

23. The method as claimed in claim 20, wherein said sponge is chitin sponge.

24. The method as claimed in claim 1, wherein said polymer is in the form of a powder.

25. The method as claimed in claim 24, wherein said powder is oxidized cellulose powder.

26. The method as claimed in claim 24, wherein said powder is gelatin powder.

27. The method as claimed in claim 24, wherein said powder is chitin powder.

28. The method as claimed in claim 1, wherein said polymer is in the form of a monofilament.

29. The method as claimed in claim 1, wherein said polymer is in the form of a film.

30. The method as claimed in claim 1, wherein said polymer is in the form of a microcapsule.

31. The method as claimed in claim 1, wherein said anti-cancer drug is an alkylating agent.

32. The method as claimed in claim 1, wherein said anti-cancer drug is a combination of cyclophosphamide, 5-fluorouracil and mitomycin.

33. The method as claimed in claim 1, wherein said anti-cancer drug is a combination of cyclophosphamide, 5-fluorouracil and bleomycin.

34. The method as claimed in claim 1, wherein said anti-cancer drug is bleomycin.

35. The method as claimed in claim 1, wherein said anti-cancer drug is mitomycin C.

36. The method as claimed in claim 1, wherein said anti-cancer drug is adriamycin.

37. The method as claimed in claim 1, wherein said anti-cancer drug is 5-fluorouracil.

38. The method as claimed in claim 1, wherein said blood coagulation factor is Factor XIII.

39. The method as claimed in claim 1, wherein said blood coagulation factor is thrombin.

40. The method as claimed in claim 1, wherein said blood coagulation factor is a combination of Factor XIII and thrombin.

41. The method as claimed in claim 1, wherein said anti-cancer drug and blood coagulation factor are fixed to the polymer by covalently bonding to the polymer.

42. The method as claimed in claims 1, 6, 16, 20, 24, 28, 29 or 30, wherein said anti-cancer drug and blood coagulation factor are fixed to the said polymer by ionically bonding to said polymer.

43. The method as claimed in claims 1, 6, 16, 20, 24, 28, 29 or 30, wherein said anti-cancer drug and blood coagulation factor are fixed to said polymer by adsorption.

44. The method as claimed in claims 1, 6, 16, 20, 24, 28, 29 or 30, wherein said anti-cancer drug and blood coagulation factor are fixed to said polymer for entrapping.

45. The method as claimed in claim 1, wherein calcium ion is additionally fixed to said polymer.

46. The method as claimed in claim 1, wherein a pharmaceutical is additionally fixed to said polymer.

47. The method as claimed in claim 46, wherein said pharmaceutical is selected from the group consisting of protease inhibitors, plasma proteins, fibronectin, antiboitics, antivirals, sulfaniamides and anti-infectives.

48. The method as claimed in claim 1, wherein said polymer is a bioabsorbable polymer and wherein said polymer is in the form of a fibrous assembly.

49. The method as claimed in claim 1, wherein said polymer is a bioabsorbable material and wherein said polymer is in the form of a sponge.

50. The method as claimed in claim 1, wherein said polymer is a bioabsorbable material and wherein said polymer is in the form of a powder.

51. The method as claimed in claim 1, wherein said polymer is a bioabsorbable material and wherein said polymer is in the form of a monofilament.

52. The method as claimed in claim 1, wherein said polymer is a bioabsorbable material and wherein said polymer is in the form of a film.

53. The method as claimed in claim 1, wherein said polymer is a bioabsorbable material and wherein said polymer is in the form of a microcapsule.

54. The method as claimed in claim 1, wherein said polymer is gelatin powder, said anti-cancer drug, and said blood coagulation factor are fixed to said polymer by ionic bonding, entrapping and adsorption, said anti-cancer drug is mitomycin C and wherein said blood coagulation factor is a combination of Factor XIII and thrombin.

* * * * *